United States Patent [19]

Goodman et al.

[11] 4,374,057

[45] Feb. 15, 1983

[54] AQUEOUS DISPERSIONS OF FREE RADICAL-GENERATING POLYMERIZATION INITIATORS

[75] Inventors: Donald Goodman, Flemington, N.J.; Mario Q. Ceprini, Cedarhurst; Samuel Hoch, Brooklyn, both of N.Y.; Marvin Koral, Warren, N.J.

[73] Assignee: Tenneco Chemicals, Inc., Piscataway, N.J.

[21] Appl. No.: 289,551

[22] Filed: Aug. 3, 1981

[51] Int. Cl.³ .............................................. B01J 31/02
[52] U.S. Cl. ..................................... 252/426; 562/599
[58] Field of Search ......................... 252/426; 562/599

[56] References Cited

U.S. PATENT DOCUMENTS

| | | | |
|---|---|---|---|
| 3,825,509 | 7/1974 | Miller | 252/426 |
| 3,988,261 | 10/1976 | Barter et al. | 252/426 |
| 4,039,475 | 8/1977 | Oosterwijk | 252/426 |
| 4,043,940 | 8/1977 | Sanchez | 252/426 |
| 4,105,584 | 8/1978 | Norbäck et al. | 252/426 |

*Primary Examiner*—Arthur P. Demers
*Attorney, Agent, or Firm*—Evelyn Berlow

[57] ABSTRACT

An aqueous dispersion of a free radical-generating polymerization initiator that is a shelf-stable liquid at temperatures at which the initiator can be stored safely comprises 10% to 50% by weight of a liquid free radical-generating polymerization initiator, 0.8% to 3% by weight of a suspending agent, 0.1% to 1.0% by weight of a wetting agent, and 0 to 50% by weight of an antifreeze additive.

15 Claims, No Drawings

AQUEOUS DISPERSIONS OF FREE RADICAL-GENERATING POLYMERIZATION INITIATORS

This invention relates to shelf-stable aqueous dispersions of free radical-generating polymerization initiators that are liquid at temperatures at which the initiator can be stored safely and to a process for their production.

Vinyl halide resins are generally prepared by suspension polymerization processes in which a monomer component that comprises a vinyl halide is polymerized in an aqueous medium in the presence of a monomer-soluble free radical-generating polymerization initiator and a suspending agent. In these processes, the initiators are usually added to the polymerization mixture as solutions in aliphatic, cycloaliphatic, or aromatic organic solvents in order to reduce the hazards involved in storing and handling the very reactive initiators and to assist in their dispersion throughout the polymerization mixture.

The addition to the polymerization mixtures of the initiators as 20% to 25% by weight solutions in organic solvents presents difficulties from an industrial point of view in that they create a potential fire or explosion hazard. In addition, it is likely that in the filtration, stripping, and drying steps of the process the organic solvents will enter water streams or the atmosphere.

In view of present safety standards relating to the handling of volatile organic solvents and to the amounts of organic solvents that may enter water systems or the atmosphere, it has become necessary to provide aqueous dispersions of the free radical-generating polymerization initiators that can be safely and conveniently stored and handled.

Several methods have been proposed for the safe storage and handling of the highly-reactive free radical-generating polymerization initiators that are liquid at low temperatures, for example, at $-20°$ C., but none has proven to be entirely satisfactory. Some of these initiators have been stored and shipped as frozen solids or as undiluted liquids under refrigeration. These methods require special handling techniques because of the highly concentrated state of the very reactive initiators. In U.S. Pat. No. 3,825,509, Miller disclosed that the hazards involved in handling the concentrated initiators can be reduced by using them in the form of aqueous dispersions that contain up to 19% by weight of an initiator, 1% to 5% by weight of polyvinyl alcohol, and 1% to 6% by weight of polyoxyethylene sorbitan monolaurate. These aqueous dispersions are not widely used in the commercial production of vinyl halide resins because they contain a relatively low concentration of the initiators and an amount of polyoxyethylene sorbitan monolaurate that may have a deleterious effect on the clarity, heat stability, water resistance, and other properties of articles prepared from the polymers. In addition, these dispersions may freeze at the temperatures at which the initiators must be stored. Solid frozen organic peroxide emulsions that comprise 30% to 75% by weight of an organic peroxide, water, and an emulsifying amount of a surfactant were disclosed by Barter et al. in U.S. Pat. No. 3,988,261. These frozen emulsions are not convenient to use in processes in which vinyl halides are polymerized in aqueous systems because they must be thawed before they can be added to the polymerization reaction mixture. Unless these emulsions are frozen in the form of small pellets or cubes, it is difficult to handle them and to measure accurately the amount of the emulsion that contains the amount of the initiators required to promote the polymerization reaction.

This invention relates to aqueous dispersions of liquid free radical-generating polymerization initiators that are shelf-stable, mobile liquids that can be safely and conveniently measured and pumped into polymerization reaction vessels and dispersed throughout the aqueous polymerization medium at the low temperatures at which the very reactive initiators must be maintained to minimize both the loss of assay from slow decomposition and the hazard of an autoaccelerative decomposition. These aqueous dispersions, which contain a moderate to high concentration of a liquid polymerization initiator, exhibit negligible phase separation and/or solidification when stored for a week or more at the low temperatures that are necessary for the safe storage of the initiators.

The shelf-stable, mobile aqueous dispersions of this invention contain from 10% to 50% by weight and preferably 20% to 30% by weight of a free radical-generating initiator that is liquid at temperatures of $-20°$ C. or lower dispersed in an aqueous phase that contains small amounts of a suspending agent and a wetting agent. When they contain liquid initiators that must be stored at temperatures below 0° C., the aqueous dispersions also contain an antifreeze additive that prevents phase separation and/or solidification of the dispersions during low temperature storage.

The aqueous dispersions of liquid free radical-generating polymerization initiators of this invention are as effective as the initiators per se and as solutions of these initiators in organic solvents in promoting the polymerization of vinyl halides and other olefinic monomers in aqueous systems by conventional polymerization techniques. Because they contain only small amounts of wetting agents, their use does not adversely affect either the polymerization process or the properties of the polymers produced. The use of the aqueous dispersions of this invention makes possible safe and convenient handling and storage of the very reactive and hazardous initiators as well as more quantitative and safer introduction of these initiators into polymerization reaction vessels.

The free radical-generating polymerization initiators that may be present in the aqueous dispersions of this invention include organic peroxyesters, organic peroxydicarbonates, diacyl peroxides, and acyl sulfonyl peroxides that are liquid at the temperatures at which they can be stored safely, preferably at $-20°$ C. Illustrative of these initiators are tert.butyl peroctoate, tert.butyl peroxyneodecanoate, tert.butyl peroxypivalate, tert.butyl peracetate, tert.butyl perbenzoate, tert.amyl peroxyneodecanoate, tert.amyl peroxyoctoate, tert.amyl peroxy-2-ethylhexanoate, α-cumyl peroxypivalate, di-(isopropyl) peroxydicarbonate, di-(sec.butyl) peroxydicarbonate, di-(2-ethylhexyl)peroxydicarbonate, di-(4-tert.butyl cyclohexyl)peroxydicarbonate, diisobutyl peroxide, acetyl peroxide, acetyl sec.butyl sulfonyl peroxide, acetyl sec.hexyl sulfonyl peroxide, acetyl cyclopentyl sulfonyl peroxide, acetyl cyclohexyl sulfonyl peroxide, and the like. A single initiator or a mixture of two or more of these initiators may be present in the aqueous dispersions.

The suspending agents that are used in the preparation of the aqueous dispersions of this invention are preferably those that are commonly used in the suspension polymerization of vinyl halides in an aqueous medium. They include water-soluble cellulose derivatives, such as methylcellulose, hydroxymethylcellulose, hydroxyethylcellulose, and hydroxypropylcellulose; gelatin; polyvinyl alcohol; starch; methyl vinyl ether-maleic anhydride copolymers; vinyl acetate-maleic anhydride copolymers; metal salts of carboxymethylcellulose and polyacrylic acids; and mixtures thereof. The useful wetting agents include nonionic surfactants, anionic surfactants, and mixtures of nonionic and anionic surfactants. Illustrative of the nonionic surfactants that can be used are polyoxyethylene alkyl ethers, polyoxyethylene alkyl esters, polyoxyethylene alkyl aryl ethers, sorbitan alkyl esters, polyoxyethylene-propylene glycol ethers, polyoxyethylene-sorbitan alkyl esters, fatty acid monoglycerides, and mixtures thereof. The anionic surfactants are exemplified by fatty acid soaps, such as sodium oleate and ammonium laurate; sulfates, such as sodium lauryl sulfate and ammonium lauryl sulfate; alkyl aryl sulfonates, such as dodecylbenzene sodium sulfonate and dodecylnaphthalene sodium sulfonate; dialkylsulfosuccinates, such as dioctyl sulfosuccinate; alkyl sulfonates; and mixtures thereof. The preferred wetting agents and nonionic surfactants derived from the ethylene oxide adducts of alkylphenols, for example, the Triton series of surfactants that is marketed by Rohm and Haas Co. and the Igepal CO series of surfactants that is marketed by GAF Corp. and the polyoxyethylene sorbitan alkyl esters, for example, the Tween series of surfactants that is marketed by ICI America Inc.

The antifreeze additive that is used when the polymerization initiator must be maintained at temperatures below 0° C. is usually an alcohol having from 1 to 3 carbon atoms, such as methanol, ethanol, isopropanol, ethylene glycol, propylene glycol, and mixtures thereof. It is preferably either methanol or ethylene glycol.

The aqueous dispersions of this invention are prepared by adding a liquid free radical-generating polymerization initiator or a solution of a liquid initiator in an organic solvent to an aqueous solution that contains a suspending agent, a wetting agent, and, optionally, an antifreeze additive and agitating the resulting mixture vigorously to form a uniform liquid dispersion that has excellent shelf stability at the temperatures at which the initiators can be stored safely.

In a preferred embodiment of the invention, stable aqueous dispersions are formed by adding a liquid initiator to an aqueous solution that contains an antifreeze additive that is methanol or ethylene glycol, a suspending agent that is a cellulose ether, and a wetting agent that is a nonylphenoxypoly(ethyelene oxy) ethanol derivative having an HLB (Hydrophile-Lipophile Balance) value in the range of 6 to 10 and subjecting the resulting mixture to vigorous agitation.

In another preferred embodiment of the invention, the liquid initiator is added to an aqueous solution that contains a suspending agent, a wetting agent, and an antifreeze additive as a solution that contains from 20% to 90% by weight, preferably 40% to 80% by weight, of the initiator in an organic solvent, such as mineral spirits, benzene, toluene, xylene, cyclohexane, dimethyl phthalate, diethyl maleate, and mixtures thereof. When the initiator is added as a solution in an organic solvent, optimum results have been obtained when the wetting agent in the aqueous solution to which the initiator solution was added was a polyoxyethylene sorbitan alkyl ester having an HLB (Hydrophile-Lipophile Balance) value in the range of 10 to 17, the suspending agent was a cellulose ether, preferably methylcellulose, and the antifreeze additive was methanol or ethylene glycol.

The shelf-stable aqueous dispersions of this inventon may contain from 10% to 50% by weight of a free radical-generating polymerization initiator that is liquid at temperatures at which it can be stored safely, from 0.8% to 3.0% by weight of a suspending agent, from 0.1% to 1.0% by weight of a wetting agent, and from 0 to 50% by weight of an antifreeze additive. They preferably contain 20% to 30% by weight of a liquid free radical-generating polymerization initiator that is liquid at $-20°$ C., from 1% to 2% by weight of a suspending agent, from 0.1% to 0.5% by weight of a wetting agent, and either from 15% to 20% by weight of methanol or from 20% to 25% by weight of ethylene glycol. When the liquid initiator is added to the aqueous system as a solution in an organic solvent, the resulting dispersion may contain from 2% to 15% by weight and preferably from 5% to 10% by weight of the organic solvent.

The invention is further illustrated by the following examples. In these examples, all parts are parts by weight and all percentages are percentages by weight.

EXAMPLE 1

A mixture of 58.3 parts of water and 15 parts of methanol was agitated while 0.2 part of nonylphenoxypoly(ethyleneoxy)ethanol (GAF's Igepal CO-430, HLB-8.8) was added to it. The solution was then agitated vigorously and maintained at 21°-24° C. while 1.5 parts of methylcellulose (Dow's Methocel) was added to it over a period of one hour. When the addition was complete, the solution was stirred at 20°-22° C. for an additional 30 minutes. Then 25 parts of bis-(2-ethylhexyl)peroxydicarbonate was added, and the mixture was vigorously agitated for 15 minutes to form a uniform dispersion that contained 25% of the initiator, 15% of methanol, 1.5% of suspending agent, and 0.2% of wetting agent. When stored at $-15°$ C. to $-10°$ C., it remained a stable, uniform liquid dispersion for more than 2 weeks.

EXAMPLES 2-5

The procedure described in Example 1 was repeated using different amounts of methylcellulose and wetting agent. The materials used in the preparation of the dispersions are shown in Table I.

TABLE I

| Ex. No. | Water (parts) | Methanol (parts) | Wetting Agent (part) | Methylcellulose (parts) | Bis(2-ethylhexyl) peroxydicarbonate (parts) |
|---|---|---|---|---|---|
| 2 | 57.8 | 15 | 0.2 | 2.0 | 25 |
| 3 | 57.0 | 15 | 1.0 | 2.0 | 25 |
| 4 | 58.0 | 15 | 0.5 | 1.5 | 25 |
| 5 | 57.5 | 15 | 1.0 | 1.5 | 25 |

In each case, the dispersion obtained was stable for more than a week when stored at $-15°$ to $-10°$ C.

EXAMPLES 6-8

The procedure described in Example 1 was repeated except that ethylene glycol was used instead of methanol. The materials used in the preparation of the dispersions are shown in Table II.

TABLE II

| Ex. No. | Water (parts) | Ethylene glycol (parts) | Wetting Agent (part) | Methyl-cellulose (parts) | Bis(2-ethylhexyl) peroxydicarbonate (parts) |
|---|---|---|---|---|---|
| 6 | 53 | 20 | 0.5 | 1.5 | 25 |
| 7 | 48 | 25 | 0.5 | 1.5 | 25 |
| 8 | 53.3 | 20 | 0.2 | 1.5 | 25 |

These dispersions remained stable uniform liquids for more than a week when stored at −15° to −10° C.

EXAMPLE 9

A mixture of 50 parts of water, 15 parts of methanol, and 0.2 part of polyoxyethylene sorbitan monolaurate which had an HLB of 13.3 (ICI America's Tween 21) was vigorously agitated at 21°–24° C. while 1.5 parts of methylcellulose (Dow's Methocel) was added to it over a period of one hour. When the addition was complete, the solution was stirred at 20°–22° C. for an additional 30 minutes. Then 33.3 parts of a 25% solution of bis(2-ethylhexyl)peroxydicarbonate in mineral spirits (Noury Chemical's Trigonox EHP C-75) was added, and the mixture was agitated vigorously for 15 minutes to form a uniform dispersion that contained 25% of the initiator, 15% of methanol, 1.5% of suspending agent, 8.3% of mineral spirits, and 0.2% of wetting agent. When stored at −15° to −10° C., it remained a stable, uniform liquid dispersion for more than 2 weeks.

EXAMPLES 10–14

The procedure described in Example 9 was repeated using different amounts of methylcellulose and the initiator solution. The materials used in the preparation of the dispersions are shown in Table III.

TABLE III

| Ex. No. | Water (parts) | Methanol (parts) | Wetting Agent (part) | Methyl-cellulose (parts) | Mineral Spirits (parts) | Bis(2-ethylhexyl) peroxidicarbonate (parts) |
|---|---|---|---|---|---|---|
| 10 | 50.00 | 15 | 0.2 | 1.50 | 8.3 | 25 |
| 11 | 50.25 | 15 | 0.2 | 1.25 | 8.3 | 25 |
| 12 | 50.50 | 15 | 0.2 | 1.00 | 8.3 | 25 |
| 13 | 56.60 | 15 | 0.2 | 1.50 | 6.7 | 20 |
| 14 | 56.85 | 15 | 0.2 | 1.25 | 6.7 | 20 |

In each case, the dispersion obtained remained a stable liquid when stored at −15° to −10° C. for more than a week.

EXAMPLES 15 AND 16

The procedure described in Example 9 was repeated except that ethylene glycol was used instead of methanol and different amounts of the initiator solution were used. The materials used in the preparation of the dispersions are shown in Table IV.

TABLE IV

| Ex. No. | Water (parts) | Ethylene glycol (parts) | Wetting Agent (part) | Methyl-cellulose (parts) | Mineral Spirits (parts) | Bis(2-ethylhexyl) peroxidicarbonate (parts) |
|---|---|---|---|---|---|---|
| 15 | 45.0 | 20 | 0.2 | 1.5 | 8.3 | 25 |
| 16 | 51.6 | 20 | 0.2 | 1.5 | 6.7 | 20 |

Each of the dispersions remained a stable uniform liquid when stored at −15° to −10° C. for more than a week.

EXAMPLE 17

A series of vinyl halide resins was prepared by a standard suspension procedure using as the initiator either one of the products of Examples 1–16 or a 25% solution of bis(2-ethylhexyl)peroxydicarbonate in mineral spirits. All of the resins prepared had equivalent color, static and dynamic Brabender heat stability, and other physical properties.

What is claimed is:

1. An aqueous dispersion of a free radical-generating polymerization initiator that is a shelf-stable liquid at temperatures at which the initiator can be stored safely comprising
   a. 10% to 50% by weight of a free radical-generating polymerization initiator that is liquid at temperatures at which it can be stored safely,
   b. 0.8% to 3% by weight of a suspending agent,
   c. 0.1% to 1.0% by weight of a wetting agent selected from the group consisting of anionic surfactants, nonionic surfactants, and mixtures thereof,
   d. 0 to 50% by weight of an antifreeze additive that is an alcohol having 1 to 3 carbon atoms, and
   e. 2% to 15% by weight of an organic solvent.

2. An aqueous dispersion of a free radical-generating polymerization initiator as defined in claim 1 that contains 5% to 10% by weight of an organic solvent.

3. An aqueous dispersion of a free radical-generating polymerization initiator as defined in claim 1 wherein the organic solvent is a hydrocarbon.

4. An aqueous dispersion of a free radical-generating polymerization initiator as defined in claim 1 wherein the organic solvent is mineral spirits.

5. An aqueous dispersion of a free radical-generating polymerization initiator as defined in claim 1 that comprises
   a. 20% to 30% by weight of said free radical-generating polymerization initiator,
   b. 1% to 2% by weight of said suspending agent,
   c. 0.1% to 0.5% by weight of said wetting agent,
   d. 10% to 20% by weight of methanol, and
   e. 5% to 10% by weight of mineral spirits.

6. An aqueous dispersion of a free radical-generating polymerization initiator as defined in claim 1 that comprises
   a. 20% to 30% by weight of said free radical-generating polymerization initiator,
   b. 1% to 2% by weight of said suspending agent,
   c. 0.1% to 0.5% by weight of said wetting agent,
   d. 20% to 30% by weight of ethylene glycol, and
   e. 5% to 10% by weight of mineral spirits.

7. An aqueous dispersion of a free radical-generating polymerization initiator as defined in claim 1 wherein the initiator is bis-(2-ethylhexyl)peroxydicarbonate.

8. An aqueous dispersion of a free radical-generating polymerization initiator as defined in claim 1 wherein the suspending agent is a cellulose ether.

9. An aqueous dispersion of a free radical-generating polymerization initiator as defined in claim 1 wherein the suspending agent is methylcellulose.

10. The process for the production of aqueous dispersions of free radical-generating polymerization initiators that are shelf-stable liquids at temperatures at which the initiators can be stored safely that comprises the steps of a. forming a solution that contains from 20% to 90% by weight of a free radical-generating polymerization initiator that is liquid at temperatures at which it can be stored safely in an organic solvent, b. adding said solution to an aqueous medium that comprises a suspending agent, a wetting agent selected from the group consisting of anionic surfactants, nonionic surfactants, and mixtures thereof, and an antifreeze additive that is an alcohol having 1 to 3 carbon atoms to form an aqueous suspension that comprises 10% to 50% by weight of said initiator, 0.8% to 3% by weight of said suspending agent, 0.1% to 1.0% by weight of said wetting agent, up to 50% by weight of the antifreeze additive, and 2% to 15% by weight of the organic solvent, and c. subjecting said aqueous suspension to vigorous agitation to form a shelf-stable liquid aqueous dispersion of said initiator.

11. The process of claim 10 wherein the solution formed in Step a. contains from 50% to 80% by weight of said liquid initiator.

12. The process of claim 10 wherein the suspension formed in Step b. comprises 20% to 30% by weight of said initiator, 1% to 2% by weight of said suspending agent, 0.1% to 0.5% by weight of said wetting agent, 10% to 20% by weight of methanol, and 5% to 10% by weight of organic solvent.

13. The process of claim 10 wherein the suspension formed in Step b. comprises 20% to 30% by weight of said initiator, 1% to 2% by weight of said suspending agent, 0.1% to 0.5% by weight of said wetting agent, 20% to 30% by weight of ethylene glycol, and 5% to 10% by weight of the organic solvent.

14. The process of claim 10 wherein the organic solvent used in forming the solution in Step a. is mineral spirits.

15. The process of claim 10 wherein the free radical-generating polymerization initiator is bis-(2-ethylhexyl)-peroxydicarbonate.

* * * * *